United States Patent
Banko

(10) Patent No.: US 10,179,068 B2
(45) Date of Patent: Jan. 15, 2019

(54) SURGICAL HAND PIECE WITH ROTATABLE DUAL LUMEN WORK TIP

(71) Applicant: SURGICAL DESIGN CORPORATION, Armonk, NY (US)

(72) Inventor: William Banko, Armonk, NY (US)

(73) Assignee: SURGICAL DESIGN CORPORATION, Armonk, NY (US)

( * ) Notice: Subject to any disclaimer, the term of this patent is extended or adjusted under 35 U.S.C. 154(b) by 801 days.

(21) Appl. No.: 14/292,459

(22) Filed: May 30, 2014

(65) Prior Publication Data

US 2014/0276369 A1 Sep. 18, 2014

Related U.S. Application Data

(63) Continuation-in-part of application No. 14/142,555, filed on Dec. 27, 2013, which is a
(Continued)

(51) Int. Cl.
*A61F 9/007* (2006.01)
*A61M 1/00* (2006.01)
*A61B 17/32* (2006.01)

(52) U.S. Cl.
CPC ....... *A61F 9/00745* (2013.01); *A61M 1/0064* (2013.01); *A61B 2017/320084* (2013.01); *A61B 2217/005* (2013.01); *A61B 2217/007* (2013.01)

(58) Field of Classification Search
CPC .......... A61M 16/0833; A61M 16/0858; A61M 16/0875; A61M 16/1095; A61M 16/16; A61M 16/20; A61M 16/208; A61M 1/0064; A61M 1/008; A61M 1/0086; A61M 1/3661; A61M 2025/0004; A61M 2025/0008; A61M 2025/00; A61M 2025/015; A61M 2025/0681; A61M 2025/09125; A61M 2025/1054; A61M 2025/1068; A61M 2025/1077; A61M 2025/1084; A61M 2025/1086;
(Continued)

(56) References Cited

U.S. PATENT DOCUMENTS

| 4,425,115 A | 1/1984 | Wuchinich |
| 4,504,264 A * | 3/1985 | Kelman .............. A61F 9/00745 |
| | | 604/22 |

(Continued)

OTHER PUBLICATIONS

Non-Final Office Action in corresponding U.S. Appl. No. 14/142,555, dated Feb. 12, 2016.
(Continued)

*Primary Examiner* — Brandy S Lee
(74) *Attorney, Agent, or Firm* — Leason Ellis LLP

(57) ABSTRACT

A surgical hand piece has a connecting body having first and second passages detachably connected to first and second lumens which are used in the eye for phacoemulsification procedures and/or cleanup of the eye capsule after the procedure. The lumens receive or discharge fluid from first and second fluid sources. A work tip supporting the first and second tubes can be rotated so as to change the function of the first and second tubes from aspiration to irrigation and vice versa. As an alternative, a sleeve holding the fluid sources can be rotated so as to change the function of the first and second tubes from aspiration to irrigation and vice versa.

23 Claims, 13 Drawing Sheets

Related U.S. Application Data continuation-in-part of application No. 12/215,315, filed on Jun. 26, 2008, now Pat. No. 8,641,658.

(58) Field of Classification Search
CPC ...... A61M 2025/109; A61M 2029/025; A61M 2037/0007; A61M 2039/0009; A61B 2217/005; A61B 2217/007; A61B 2017/320084; A61F 9/00745
See application file for complete search history.

(56) References Cited

U.S. PATENT DOCUMENTS

| | | | |
|---|---|---|---|
| 4,551,130 A * | 11/1985 | Herbert | A61M 3/0233 604/247 |
| 4,735,604 A * | 4/1988 | Watmough | A61B 17/22012 604/22 |
| 4,750,902 A | 6/1988 | Wuchinich | |
| 5,084,013 A | 1/1992 | Takase | |
| 5,254,082 A * | 10/1993 | Takase | A61B 17/320068 604/119 |
| 5,817,099 A | 10/1998 | Skolik et al. | |
| 6,007,511 A | 12/1999 | Prywes | |
| 6,282,442 B1 | 8/2001 | DeStefano et al. | |
| 6,309,347 B1 | 10/2001 | Takashi | |
| 7,083,589 B2 | 8/2006 | Banko et al. | |
| 7,503,895 B2 | 3/2009 | Rabiner | |
| 2002/0022796 A1 | 2/2002 | Lawrence et al. | |
| 2002/0161326 A1 | 10/2002 | Sussman et al. | |
| 2003/0176791 A1 * | 9/2003 | Rabiner | A61B 17/22012 600/439 |
| 2005/0085769 A1 | 4/2005 | MacMahon | |
| 2005/0267400 A1 * | 12/2005 | Haarala | A61M 1/3653 604/43 |
| 2006/0173244 A1 | 8/2006 | Boulais et al. | |
| 2008/0044790 A1 | 2/2008 | Fani | |

OTHER PUBLICATIONS

Non-Final Office Action in corresponding U.S. Appl. No. 14/142,555, dated Dec. 1, 2016.

Non Final Office Action dated Feb. 27, 2017 of U.S. Appl. No. 14/506,404.

Non Final Office Action dated Jan. 26, 2018 of U.S. Appl. No. 14/142,555.

* cited by examiner

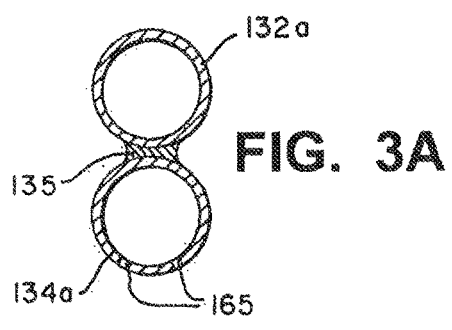
FIG. 3A
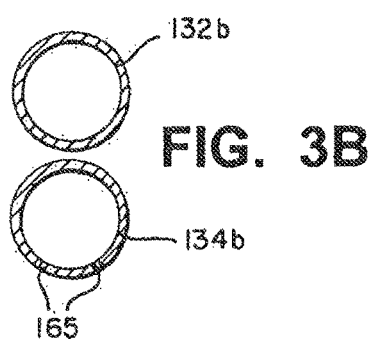
FIG. 3B
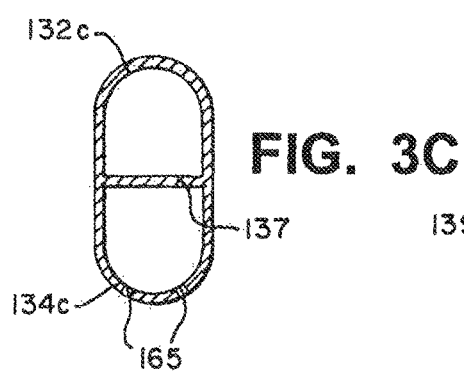
FIG. 3C
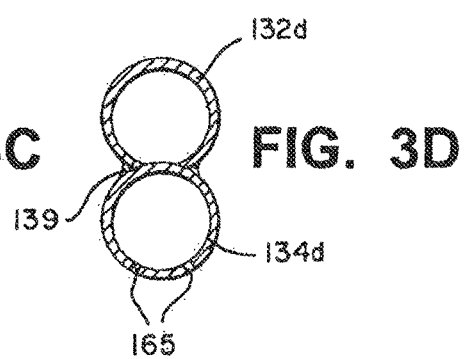
FIG. 3D
FIG. 4A
FIG. 4B
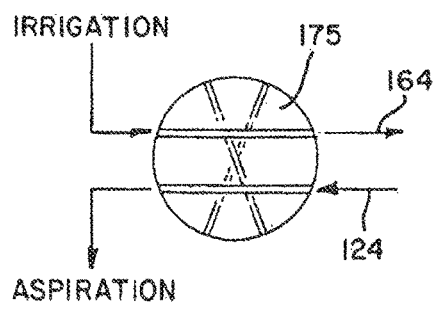
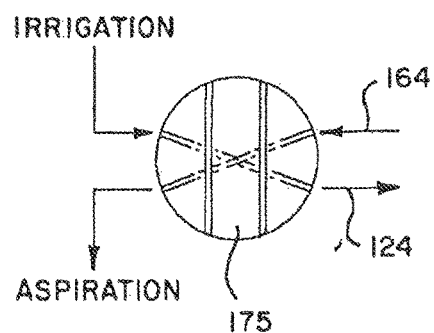

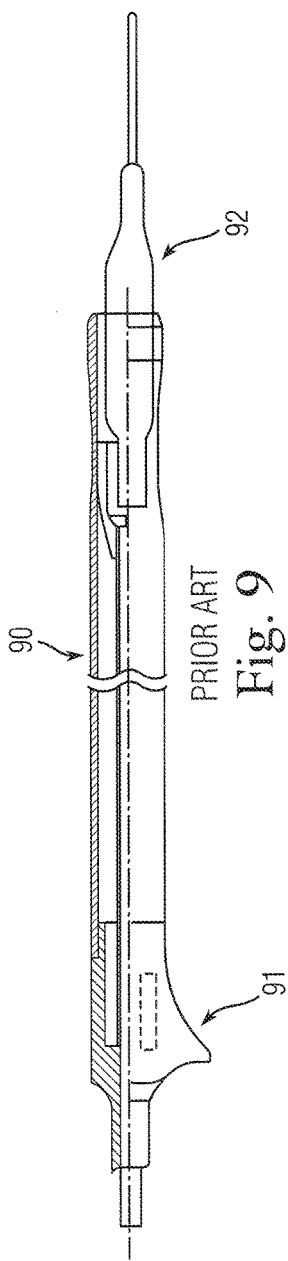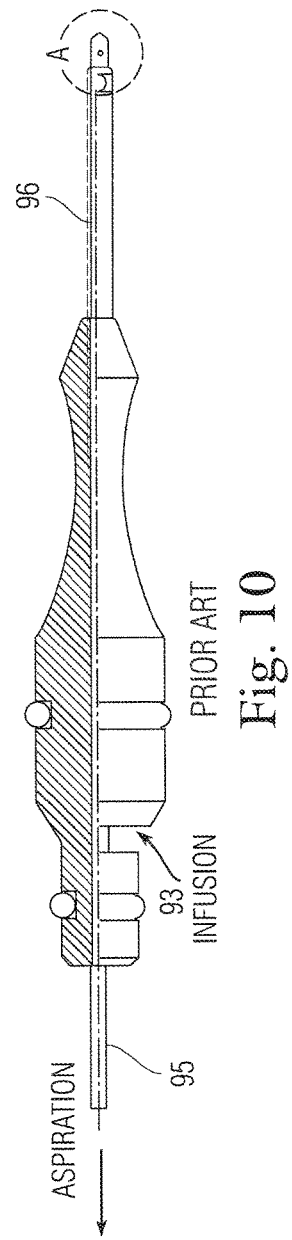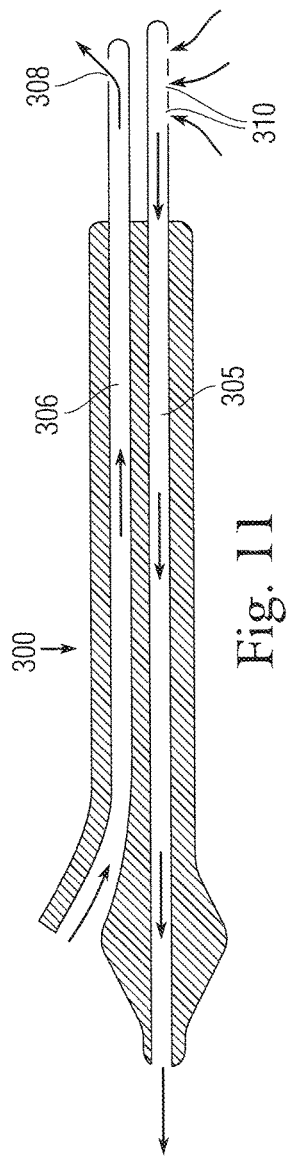

SURGICAL HAND PIECE WITH ROTATABLE DUAL LUMEN WORK TIP

CROSS-REFERENCE TO RELATED APPLICATIONS

The present application is a continuation-in-part of prior U.S. patent application Ser. No. 14/142,555 filed on Dec. 27, 2013, which in turn is a continuation-in-part of prior U.S. patent application Ser. No. 12/215,315 filed on Jun. 26, 2008 (now U.S. Pat. No. 8,641,658, which issued Feb. 4, 2014).

TECHNICAL FIELD

The present invention is generally directed to an ultrasonic surgical hand piece with a dual lumen work tip that is disposable, and can be used for the removal of cataracts from the eye of a patient by phacoemulsification.

BACKGROUND OF THE INVENTION

The use of ultrasonic instruments in surgical applications is well known. One widely used type of instrument is an ultrasonic hand piece that is used in ophthalmic applications, such as in the removal of cataracts from the eye by phacoemulsification.

FIG. 6 depicts one such type of prior art ultrasonic hand piece as shown in U.S. Pat. No. 4,504,264 of Kelman. This hand piece has a housing 10 of, for example, plastic or metal, within which is supported a transducer means 11 for generating mechanical vibrations upon excitation with an alternating-current electrical signal. The transducer 11 is shown as a magnetostrictive transducer with an electrical coil 12 wound about a stack of metal laminations so that longitudinal mechanical vibrations are produced. The transducer can also be of the piezoelectric type. There is a connecting body 16 of, for example, titanium, having a reduced diameter distal end portion, which also can be an attached separate portion. The connecting body forms an acoustic impedance transformer for conveying the longitudinal vibrations of the transducer 11 for application to an operative tool or working tip 14 connected to the distal end of the connecting body 16.

The work tip 14 is at least partially external of the housing 10. It is connected, such as by a screw thread, to the narrowed distal end of the connecting body 16 so as to be coupled to the transducer 11. As a result, the work tip is longitudinally vibrated by the transducer. The working tip 14 is an elongated, hollow tip of a suitable metal, such as titanium, that is capable of supporting ultrasonic vibrations. It has a distal end of a desired shape to be placed against the tissue to be removed. The work tip 14 has a base portion 15 in threaded engagement with the distal end of the connecting body 16. The tip 14 can be interchanged by use of the screw threads.

The distal end of the tip 14 is shown surrounded by a sleeve 17, which may be made of a material such as silicone, whose proximal end 18 is supported in threaded engagement on a reduced diameter end of the housing 10. If desired, the proximal end of sleeve 17 can be engaged more proximally along the length of the housing 10. The connecting body 16 has two elastomeric 0-rings 19, 20 on its outer surface. These provide a fluid-tight seal between the connecting body 16 and the transducer means 11. A plurality of screws 51 are shown disposed around the axis of the housing 10 for preventing longitudinal displacement (other than vibration) or rotational movement of the vibratory structure within the housing and also for radial centering of the vibratory structure within the housing. Other types of conventional mounting arrangements can be used.

The hand piece also illustratively has electrical input terminals 40, 41 for applying a suitable electrical signal to the magnetostrictive transducer 11. Cooling water is shown provided inside the housing 10 from an inlet 42 to an outlet 43 and within a chamber between 0-ring 19 and a grommet 50 for circulation around the transducer. This is not always necessary and is not used in most present day hand pieces.

The sleeve 17 around the tip 14 forms a first fluid passage 21 between the tip 14 and the sleeve for an infusion/irrigation fluid. An inlet 22 is provided on the housing or sleeve distally of the 0-ring 20 for supplying the irrigation fluid to the passage 21 from a fluid supply, e.g., a bag of saline solution (not shown).

A passage 23 is formed through the connecting body 16 that is in communication with a central passage 25 of the work tip 14. An outlet 24 on the housing or sleeve receives a suction (aspiration) force that is applied to the passage 23 in the connecting body and the central passage 25 in the work tip. A chamber 31 is formed between the spaced 0-rings 19, 20 on the body 16 and the housing 10, with which the aspiration force from outlet 24 communicates. Thus the aspiration force is from the source (e.g., a suction pump not shown), into the chamber 31 between the 0-rings, through the passage 23 in the connecting body and the passage 25 in the work tip 14. Tissue that is emulsified by the work tip is aspirated from the operating site by the aspiration flow force. In particular, saline solution introduced into the eye through fluid passage 21 and tissue displaced by the vibration force of the tip 14, is drawn into the distal end of passage 25 and passes out of the hand piece through outlet 24. It should be noted that passage 25 is located concentrically within passage 21.

As indicated, other apparatus (not shown) for use with the hand piece include the suction pump for producing the aspiration fluid (suction), the treatment fluid supply (infusion/irrigation fluid, such as a saline liquid), an oscillator for applying an electrical signal to the vibratory structure and control apparatus therefore. All of these are of conventional construction.

Considering now the operation of the hand piece of FIG. 6. When an electrical signal having a frequency of, for example, 40,000 cycles/second is applied to the coil 12 around the magnetostrictive transducer 11, the transducer 11 vibrates longitudinally at 40,000 cycles per second, thereby vibrating the connecting bodies 13, 16 and the work tip 14. Treatment fluid is supplied through inlet 22 and fluid passage 21 to bathe the tissue in the operating site region around the working tip 14. Suction force is applied through inlet 24 and passage 23 to the working tip 14 passage 25 to withdraw the tissue fragmented by the work tip along with some of the treatment fluid.

Instruments of the type described above are often used in cataract surgery in which the eye lens is removed from the eye capsule and an intra-ocular lens (IOL) is then implanted. In such a procedure before the IOL is implanted it has been found to be desirable to cleanup lens substance and lens epithelial cells (LEC's) in the capsular bag of the eye and to remove them. Doing this procedure provides a more stable and long-term fixation for certain types of IOL's in the capsular bag. One manner of accomplishing the cleanup is to use a combination of irrigation of the capsular bag interior with a liquid together with the application of low power ultrasonic energy. This dislodges the unwanted cells and substances so that they can be removed from the capsular bag by the aspiration fluid flow.

In a cleanup procedure it is advantageous if the flow of the irrigation liquid can be made more directional than would be possible using the hand piece with the outer sleeve through which the liquid flows and exits from around the work tip that produces the ultrasonic energy. It is also better if the aspiration force is lower. As a result, typically a different tip from the one illustrated in FIG. 6, which breaks up the tissue, is used for the cleanup. In fact a completely different instrument called an irrigation or infusion/aspiration (I/A) instrument is often used for this purpose. Such an instrument 90 is illustrated in FIG. 9. It has a handle 91 at one end and a work tip 92 at the other end. An enlarged view of the work tip is shown in FIG. 10. The I/A instrument work tip has concentric infusion and aspiration lumens, and typically has no ultrasonic vibration capability. The infusion fluid enters the work tip at opening 93 and is in an outer concentric lumen so that its flow surrounds the distal part of lumen 95 of the work tip. The aspirated tissue enters a small hole 94 in the distal part and is withdrawn through lumen 95. Thus, when the phacoemulsification has been completed and cleanup is to be started, the surgeon must remove the phacoemulsification tool from the eye. Then the surgeon removes the first or phacoemulsification work tip, replaces it with a different cleanup work tip and then inserts the new work tip or a separate I/A tool 90 is inserted in to the eye. This second insertion into the eye increases the possibilities of infection and trauma. Also, the A/I tool has a disadvantage in that the surgeon would have to keep inserting and withdrawing the ultrasonic work tip and the I/A tool from the eye as the process is completed, because the surgeon cannot be sure that all of the tissue has be broken up until the cleanup process has begun. As a result, this would also subject the patient to the increased possibilities of infection and trauma.

As shown in the present inventor's own U.S. Pat. No. 7,083,589, the surgical instrument may be provided with a coupler body located between the connecting body and the work tip. In such a case the aspiration fluid flow is provided from the work tip aspiration passage through the coupler to an outlet without coming into contact with the interior of the connecting body. Irrigation fluid can be provided through a portion of the housing that surrounds the proximal part of the work tip so as to form a chamber which is in communication with a separate passage in the work tip. The coupler is detachably connected to the connecting body. This allows the removal of the work tip, which becomes a single use part, so that the rest of the instrument can be reused by replacing the work tip without having to sterilize the connecting body. However, the portion of the housing surrounding the work tip and which forms the chamber for irrigation fluid, also needs to be replaced in this design.

Accordingly a need exists for a surgical hand piece that can provide both ultrasonic energy to emulsify tissue, cells and other substances which are aspirated by an aspiration fluid and an irrigation liquid that can be applied to part of the operating site being cleaned in a more directional and controlled manner. Further, it would be beneficial if the cleaning were carried out by an A/I tool without ultrasonic vibration, but had a dual lumen structure to create different kinds of cleaning irrigation patterns and force. In addition, it would be beneficial if phacoemulsification instruments with dual lumens could have their operation varied without withdrawing the instrument from the eye and/or diverting the surgeon's attention from the operating site. This would reduce the chances of infection and trauma.

SUMMARY OF THE INVENTION

In accordance with the invention a surgical hand piece is provided that can perform all of the functions of emulsification of tissue and other substances by ultrasonic energy, aspiration of such tissue and substances, and/or provide a variable directed liquid irrigation of a site that is being worked on in order to clean up the site.

The invention provides a surgical phacoemulsification hand piece that has a novel work tip having a dual separate side-by-side lumen construction, as opposed to the concentric structure of the prior art. The work tip is effectively a unit of two tubes or sections of two tubes. Hereafter the term "tube" refers to a full tube or a section of a tube with each such tube or section having its own lumen. Where sections of tubes are used, at least a portion of such sections are integrated along a common surface. One of the tubes receives the ultrasonic energy from the hand piece and its lumen forms the aspiration passage through which the emulsified tissue and other substances are removed. This tube can have any desired shape at its working end and any desired shape of aspiration opening. The irrigation liquid flows through the other tube and its end can have any number of openings or ports in any desired pattern to direct the flow of the irrigation fluid.

The novel work tip, whose lumens allow fluid to flow from proximal to distal ends and vice versa, permits switching of the tubes between aspiration and irrigation functions so that the surgeon has a work tip with different types of openings for both irrigation and aspiration functions. In different embodiments of the invention, both of the tubes of the work tip can be supplied with ultrasonic energy and either one used for aspiration or irrigation. Further, the tip may be designed so that it can be easily exchanged for a new tip and the hand piece put into service again without having to sterilize it.

The switching of the operation of the lumens can be achieved by manually switching the tubes connected to the irrigation supply and aspiration pump. However, this requires a stop in the procedure while the switch is made. As an alternative, it is proposed that the system have a rotating valve conveniently located within a console for the surgical system that may also contain the aspiration pump. In one position the valve causes irrigation fluid to flow through one lumen and aspiration fluid to be withdrawn through the other. Operation of the valve causes the irrigation and aspiration fluid flow to switch lumens.

Another embodiment mounts the lumens in the hand piece so they can be manually rotated with respect to the inlet for the irrigation fluid and outlet for the aspiration fluids. Thus, by rotating a portion of the hand piece while the work tip is still located in the eye reverses the functions of the lumens. This is beneficial because it is fast and the surgeon does not have to take his or her attention away from the operation site. In one embodiment the irrigation and aspiration fluid supply tubes rotate with respect to the lumens in the work piece, but in another embodiment the lumens rotate with respect to the tubes. In order to avoid twisting of the tubes the preferred embodiment has the lumens rotate in the hand piece.

The principles of the present invention can also be applied to an A/I instrument with no ultrasonic energy capability. In such a case, rather than have an A/I instrument with concentric lumens, at least the work tip has dual side-by-side lumens. Further, a means is provided for switching the irrigation/infusion and aspiration sources applied to each lumen. Preferably, the two lumens have at least two different irrigation patterns for cleanup. Thus, by means of a mechanism within the hand piece, the irrigation and aspiration lines can be switched and the surgeon can use a selected one of the patterns during the cleanup. These difference patterns can be achieved without the surgeon having to remove the I/A tool from the eye.

The principles of the invention have numerous advantages. For example, the invention allows for the elimination of the need for the surgeon to remove an ultrasonically-driven work tip from the operating site, such as the eye, and to insert a separate work tip or tips having irrigation/aspiration (I/A) capability, in order to perform special procedures, such as cortical and lens epithelial cleanup. Further, if an I/A tool is used according to the present invention, different irrigation patterns on each lumen can be accessed without the surgeon having to divert his attention from the eye.

BRIEF DESCRIPTION OF THE DRAWINGS

The foregoing and other objects and advantage of the present invention will become more apparent upon reference to the following specification and annexed drawings in which:

FIGS. 3A, 3B, 3C and 3D are cross-sectional views showing various forms of integrated dual lumen work tips;

FIGS. 4A and 4B are schematic views of a valve arrangement to control switching between irrigation and aspiration functions for the tubes of the work tip;

FIG. 9 is a cross section of a prior art irrigation/aspiration instrument with a removable tip;

FIG. 10 is an enlarged view of the prior art tip for the infusion/aspiration instrument of FIG. 9;

FIG. 11 is an enlarged view of a dual lumen tip for an infusion/aspiration instrument;

DETAILED DESCRIPTION OF THE INVENTION

Figure 1:
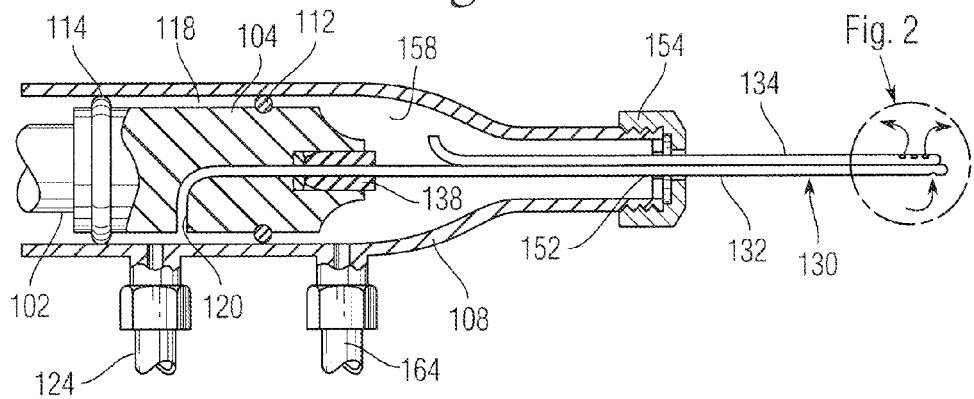
FIG. 1 is a plan view, partly in cross section, of one embodiment of the surgical hand piece of the invention.
Figure 6:
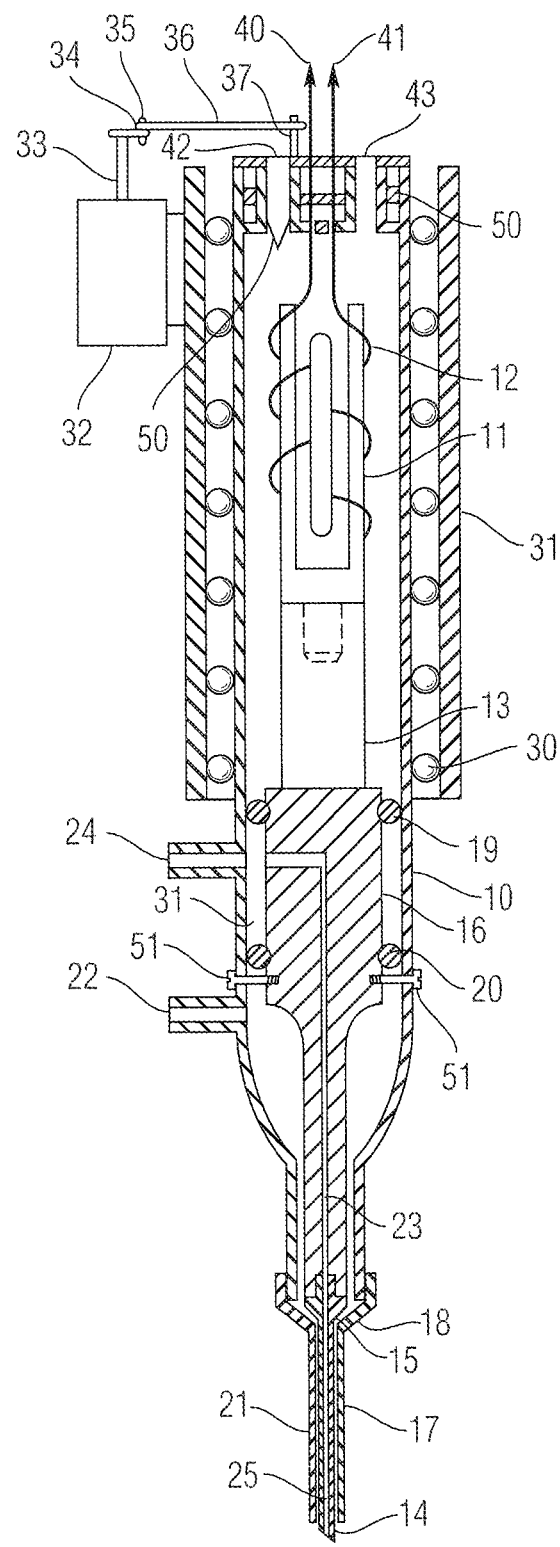
FIG. 6 is a view in cross-section of a prior art type of surgical hand piece.

FIG. 1 shows a first embodiment of the hand piece of the invention. It uses a number of the components of the prior art type of hand piece described above with respect to FIG. 6. The source of the electro-mechanical energy is shown schematically by reference number 102 and can be either the electromagnetic type as described or the piezoelectric type. It is preferred, and is conventional, that the output power of the source 102 can be controllably varied to set the ultrasonic power at the work tip distal end.

Connected to the source 102 is the connecting body 104 within a housing 108. A pair of 0-rings 112 and 114, spaced apart around the connecting body 104 and engaging the inner surface of the housing, forms a first chamber 118. The first chamber 118 receives aspiration force from a line 124 that is connected to a suitable source, such as a peristaltic pump. It is preferred that the negative (suction) pressure provided at line 124, be controllable. A flow passage 120 is formed in the connecting body 104 that communicates with the first chamber 118 and extends to the reduced diameter distal end of the connecting body 104.

A second chamber 158 is formed between the 0-ring 112 and the distal end of the housing 108. This chamber receives infusion or irrigation fluid from a line 164 that is connected to a suitable source, such as a bag of saline solution or a liquid supply having a pump. Here also, it is preferred that the volume and pressure of the fluid be controllable. The proximal end of a work tip 130 extends through the distal end of the housing 108. A flange hub 152 is connected to an intermediate point of the work tip and the flange abuts against the distal end of the housing 108 and is held against it by a threaded collar 154. This forms a fluid tight seal at the distal end of the housing and seals the second chamber 158.

The work tip 130 is a unit of two tubes or tubular sections 132 and 134. The two tubes can be of any of the types illustratively shown in FIGS. 3A-3D and described below. As illustratively shown, the proximal end of the first tube 132 has a coupling 138 that is threaded into the distal end of the connecting body 104. This places the lumen of the first tube 132 in communication with the passage 120 in the connecting body 104. Thus, the tube 132 will also be provided with ultrasonic energy from the source 102 through the connecting body 104. At the proximal end of the work tip 130 the second tube 134, which is open, is located in the housing second chamber 158 and is in communication with any fluid in this chamber. With this arrangement, there is fluid flow to or from each of the tubes 132 and 134 of the integrated work tip 130. That is, aspiration flow or liquid flow can be provided from the distal end of the first tube 132 through the passage 120 in the connecting body 104, into the first chamber 118 so as to exit at line 124 under suction from the aspiration pump. Similarly, irrigation fluid flow can be provided to line 164, to the second housing chamber 158, to the proximal end of the second tube 134 so as to exit at the distal end of tube 134. By reversing the aspiration and irrigation/infusion lines 124, 164, the flow in tubes 132, 134 can be reversed.

Figure 1A:
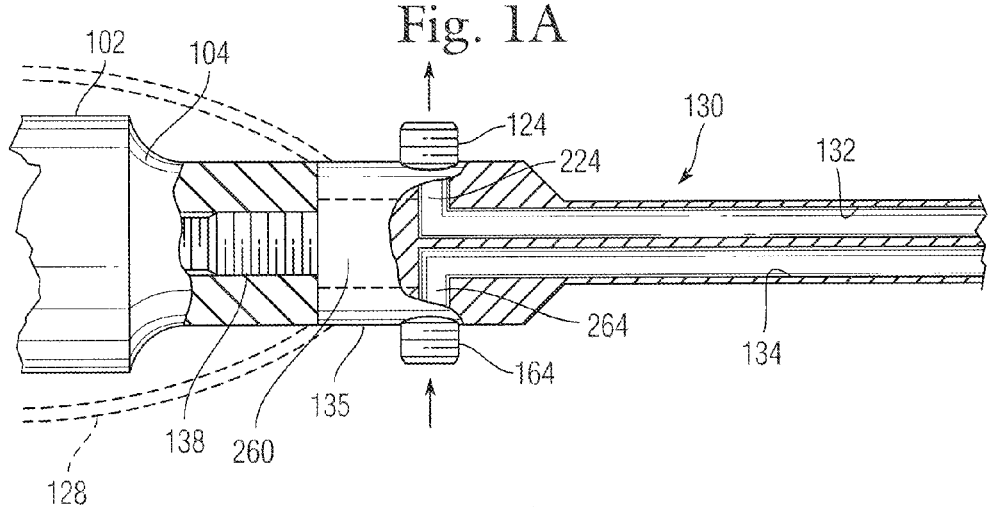
FIG. 1A is a plan view, partly in cross section, of another embodiment of the surgical hand piece of the invention.

FIG. 1A shows a further embodiment in which there is no flow passage in the connecting body 104. Here, the proximal end of the work tip 130 is a generally cylindrical hub 135 that receives the proximal ends of the tubes 132 and 134. The tubes can be any of the types described below with respect to FIGS. 3A-3D. The proximal end of the hub 135 is of reduced diameter so that it can be attached, such as by threads 138, with threads in a recess of the distal end of the connecting body 104 whose proximal end is connected to the source of ultrasonic energy 102. The hub 135 has respective passages 224 and 264 connected to the lumens of each of the tubes 132 and 134. The aspiration and irrigation fluids are withdrawn or supplied, respectively, over the lines 124 and 164 through the hub passages directly to the lumens of the two tubes. The lines 124 and 164 can be inserted directly into the hub passages 224 and 264. A housing 128 (shown in dotted line) of a suitable shape is provided over the energy source 102 and the connecting body 104. In this embodiment, both tubes 132 and 134 receive the ultrasonic energy. As described below, the fluids withdrawn from or supplied to the two tubes can be switched by using a control valve.

The work tip of FIG. 1A has an advantage in that there is no fluid flow through the connecting body 104 or any part of the instrument other than the hub 135 and the work tip 130 itself. Therefore, they are the only parts of the instrument that can become contaminated if the patient being operated on has a malady such as "mad cow/prion" disease. Also, with this arrangement, while the housing may extend over the energy source 102 and the connecting body 104, it need not extend over the hub 135. Thus no fluid chamber is formed by the housing which needs to be exchanged after use. Only the work tip 130 and hub 135 have to be sterilized after each use of the instrument or they can be treated as "disposable" and a new work tip and hub can be installed each time the instrument is used. In order to make the disposability of the work tip more practical, it can be made, at least in part, of less expensive materials. For example, a core portion 260 of the hub (shown in dotted line) extending from the connecting body 104 to the tubes 132, 134 and the tubes themselves may need to be made of a very hard material, e.g., titanium, in order to transmit vibrations of sufficient strength to affect the breakup of a cataract during its removal. However, a portion of the hub surrounding the core, the passages 224, 264 and the connectors for lines 124, 164 may be made of a less expensive material, e.g., a hard plastic, in order to reduce its cost.

Figure 2:
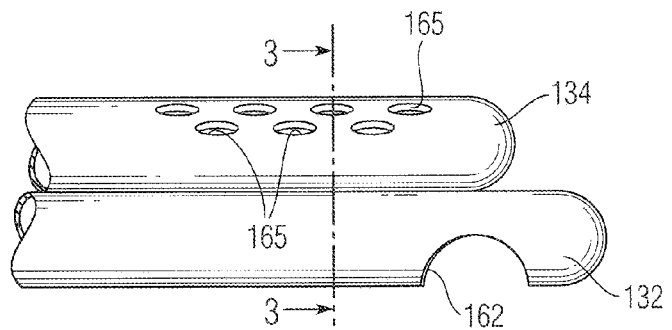
FIG. 2 is an enlarged view of the distal end of the work tip shown in FIG. 1.

FIG. 2 shows an illustrative example of the distal ends of the two tubes 132 and 134 of the work tip 130. The proximal ends of the tubes are disposed as shown in FIG. 1 or in another embodiment as shown in FIG. 5B, or by any suitable arrangement such that (a) ultrasonic energy from the transducer is coupled to the proximal end of at least one of the tubes, (b) the proximal end of at least one tube can receive the irrigation fluid and deliver it to its distal end, and (c) the proximal end of the other tube can receive the aspiration fluid from its distal end. In this example the first tube 132 is intended to be connected to receive the ultrasonic energy from the source 102 and has a scooped, or concave shaped, opening 162 near its distal end to receive the emulsified tissue that is produced by vibrations of the free end of the tube. The opening 162 can be of any desired shape and size and also can be at the extreme distal end of the tube. The second tube 134 has at least one and preferably a plurality of openings 165 through which an infusion or irrigation liquid can flow to exit at the operating site. The number of openings 165 and their pattern can be selected as desired. There can be one or more rows along the tube length. The openings 165 in tube 134 preferably are oval (elliptical) in shape as shown. Oval shaped openings 165 allow for both good dispersion of the irrigation fluid and a relatively large area over which the tissue within the eye can be swept by the irrigation fluid to dislodge cells and substances during the tissue cleaning that occurs after the cataract is broken up. The openings 165 also can have the standard circular hole configuration. As explained below, the hand piece of the invention provides for switching of the functions to be performed by the two tubes. That is, either tube can be used to perform the irrigation function or the aspiration function.

FIGS. 3A, 3B, 3C and 3D show cross-sections of tubes that can be used for the work tip 130. In FIG. 3A two fully circular tubes 132a and 134a are joined together at the area 135, such as by welding, to form a unitary structure. The joining 135 can be continuous or spaced along the lengths of the two tubes. When two complete tubes are used for the work tip they do not necessarily have to be connected together along their lengths as shown in FIG. 3A since each tube has its own lumen and does not need any part in common with the other tube to have fluid flow therein. An arrangement of two separate tubes 132b and 134b is shown in FIG. 3B. A unitary structure work tip is formed by using a hub or a similar element to hold the two tubes together as shown in FIGS. 1, 1A, 5A and 5B.

In FIG. 3C two half tube sections 132c and 134c are connected to a common central wall 137 to form a unitary structure. Here an overall somewhat elliptical tube can be divided into the two tube sections and then joined to the center common wall 137. In FIG. 3D there is a fully circular tube 134d on top of which a part of a circular tube section 132d is joined at 139 along its length, making the work tip a unitary structure. When two tube sections are used to form the work tip the proximal ends are modified (not shown) to have the appropriate shape, such as fully circular, so as to be able to perform its function such as coupling to the connecting body to receive ultrasonic energy and to receive aspiration and irrigation fluid. The distal ends also are modified to provide fluid flow from and to the aspiration and irrigation openings.

It should be understood that the two tubes 132 and 134 can be of different diameters and shapes in addition to the more symmetrical arrangements shown in the drawings. Also, the tubes can be made of any suitable material, such as titanium or any suitable material which can withstand the stress of vibration. Both tubes can be of the same material, or they can be of different materials. It also may be desirable to make one of the tubes, for example the one to which the irrigation fluid is usually applied, of a plastic material such as TEFLON®. While a tube of plastic material may not be able to transmit vibrations sufficient to break up a cataract if it receives ultrasonic energy, it can still be used to perform both the aspiration and irrigation functions depending upon which fluid is supplied to it. Further, the two tubes 132 and 134 can be of different lengths.

FIGS. 4A and 4B schematically show a valve arrangement for the supply lines 124 and 164. There is a valve 175 that receives one input from an irrigation liquid source, such as a bag of a saline solution using gravity feed or from a liquid source under controlled pressure and volume. The valve second input is from an aspiration source, such as a peristaltic pump, of controlled suction force or pressure. The valve 175 may be at any convenient location, e.g., in a console for the surgical system, not shown, and may be operated manually, by a remote control or a foot pedal. In FIG. 4A the valve 175 is in a position such that there is irrigation liquid flow is to line 164 meaning that there will be liquid in the second housing chamber 158 of FIG. 1 to be provided to the second tube 134 to flow out of its distal end. The aspiration source will be connected to the line 124 so that there will be negative pressure (suction) fluid in the first housing chamber 118 that is provided to the distal end of the first tube 132 through the passage 120 in the connecting body 104. Thus, fluid will flow from the distal end of tube 132 out of line 124 to the valve and then to the suction pump. As seen in FIG. 4B, by switching the valve 175 the conditions will be reversed so that there will be aspiration flow on line 164 causing the second tube 134 to perform an aspirating function and liquid flow in line 124 causing the first tube 132 to perform an irrigation function. Thus, the tubes 132, 134 are capable of fluid flow in either direction, depending on the function they are performing.

Figure 5A:
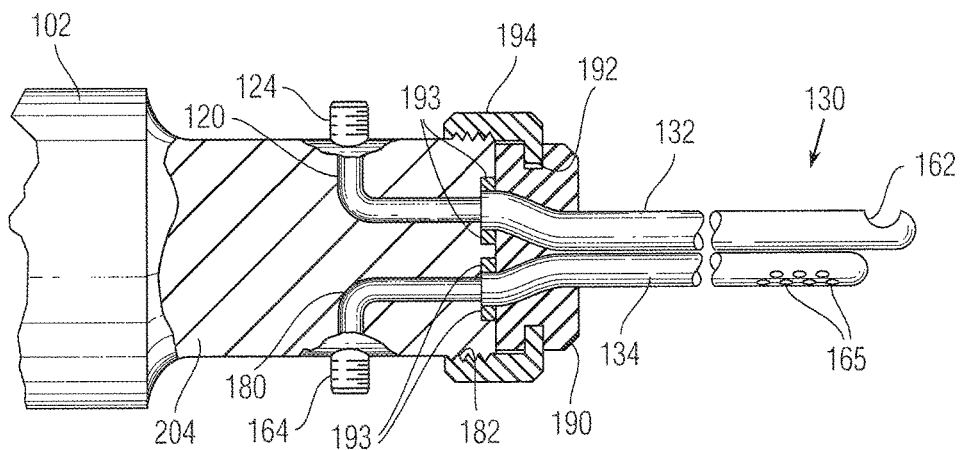
FIGS. 5A and 5B are views, partly in cross-section, of another embodiment of a surgical hand piece according to the present invention showing a change in the function of the dual lumens by rotation of the lumens within the hand piece.
Figure 5B:
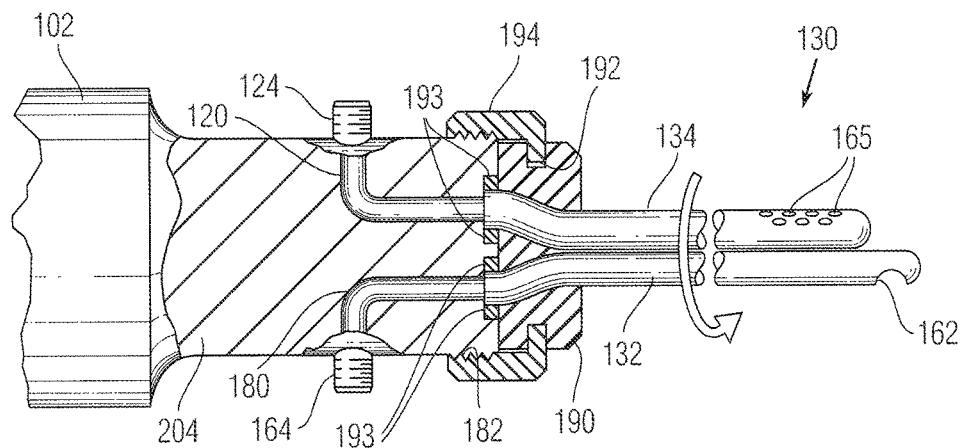

FIG. 5A shows another embodiment of the invention for coupling the work tip 130 to the hand piece. The same reference numbers are used for the same components of FIG. 1. Here there are two passages 120 and 180 in a connecting body 204. The proximal end of passage 120 is in communication with the irrigation fluid input at the supply line 124. The proximal end of passage 180 is in communication with the aspiration fluid at the supply (withdrawal) line 164. The distal ends of the two passages 120 and 180 terminate at the distal end of the connecting body 204.

There are threads 182 around the connecting body distal end. A hub 190 is around the proximal ends of the work tip tubes 132 and 134 which are bent so that the proximal ends of their lumens are parallel to the distal ends of the connecting body passages 120 and 180. A collar 194 with internal threads on its open end has its flange end rotatably mounted in a groove 192 in the hub 190. There are mating index pieces, such as mating grooves and ribs or pins (not shown), on the opposing faces of the connecting body 204 distal end and the hub 190 so that the proximal end of the lumen of tube 132 will be aligned with the distal end of connecting body passage 120 and the proximal end of the lumen of tube 134 will be aligned with the distal end of passage 180. Other types of alignment pieces and markings can be used. When the tubes and connecting body are properly aligned the collar 194 is tightened on the connecting body threads 182 and the lumens at the proximal ends of tubes 132 and 134 will be brought into fluid communication with the distal ends of the connecting body passages 120 and 180. 0-rings 193 are provided in the connecting body at the distal ends of passages 120 and 180 to make the communication fluid tight.

In this embodiment of the invention, both of the tubes 132, 134 receive the ultrasonic energy from the source 102. The valve 175 of FIG. 4 can be used with the hand piece of FIG. 5A to switch the fluid flow from the sources 124 and 164 to the lumens of tubes 132 and 134 of the integrated work tip. Since both tubes 132 and 134 receive ultrasonic energy the emulsification of tissue and its aspiration can take place through either one in addition to each tube being able to supply irrigation liquid through the different types and shapes of openings at the distal ends of the tubes.

As an alternative, rather than switching the valve 175, which may be, for example, located in the surgical console, the dual lumen tubes 132, 134 are made so that their proximal ends are located in a circular groove in the front face of the connecting body 204. See FIG. 5B. In order to accomplish this, the tubes and the hub 190 are rotated 180° so that tube 132 instead of being connected to channel 120 as shown in FIG. 5A, is connected to channel 180 as shown in FIG. 5B. See the arrow. The surgeon can manually effect this rotation, perhaps by first loosing collar 194. In such an arrangement the O-rings 193 are circular seals located in the groove in the face of the connecting body 204 to prevent leakage of the infusion and aspiration fluids.

Figure 7A:
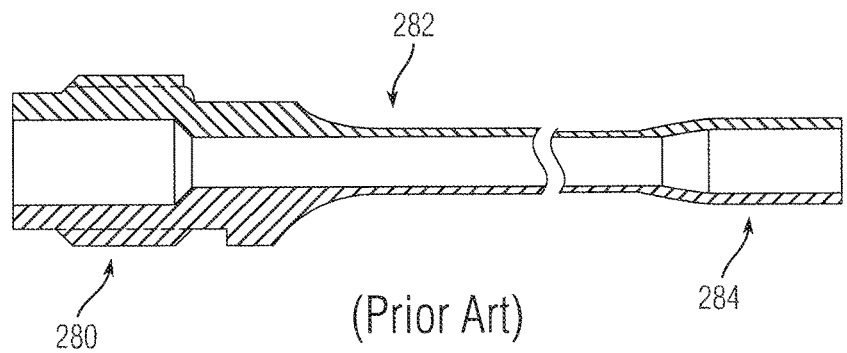
FIG. 7A is a cross-sectional view of one type of a prior art phacoemulsification work tip that can be used for one of the lumens.
Figure 7B:
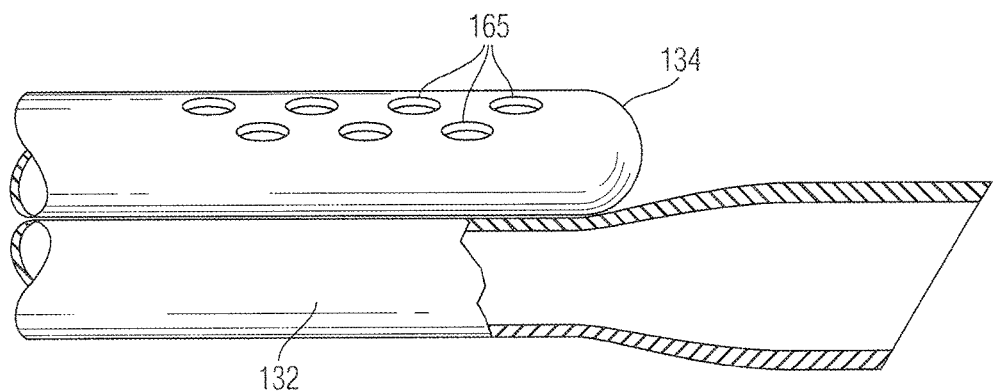
FIG. 7B shows that work tip located on a dual lumen work tip according to the invention.

FIG. 7A shows a prior art phacoemulsification tip known as the "Cobra Tip." It can be used as the aspiration lumen, e.g., lumen 132, in place of the opening 162 in order to affect a very efficient breakup of the cataract. See FIG. 7B. The portion 280 of the tip to the right is connected to the lumen. Notice that the center part 282 tapers down before and enlarged end part 284. This shape provides a very efficient transfer of ultrasonic force to the cataract. It should be noted that not only does the outer diameter expand, but the internal diameter also flares out toward the working end as shown in the cross section in FIG. 7B. This funnel design can grab and emulsify more of the cataract than a straight lumen. Further, the reduced outer diameter in the center part 282 helps to accommodate a bubble suppression sleeve to prevent bubbles in the infusion fluid. See U.S. Pat. No. 5,242,385 of Strukel, which is incorporated herein by reference in its entirety.

Figure 8A:
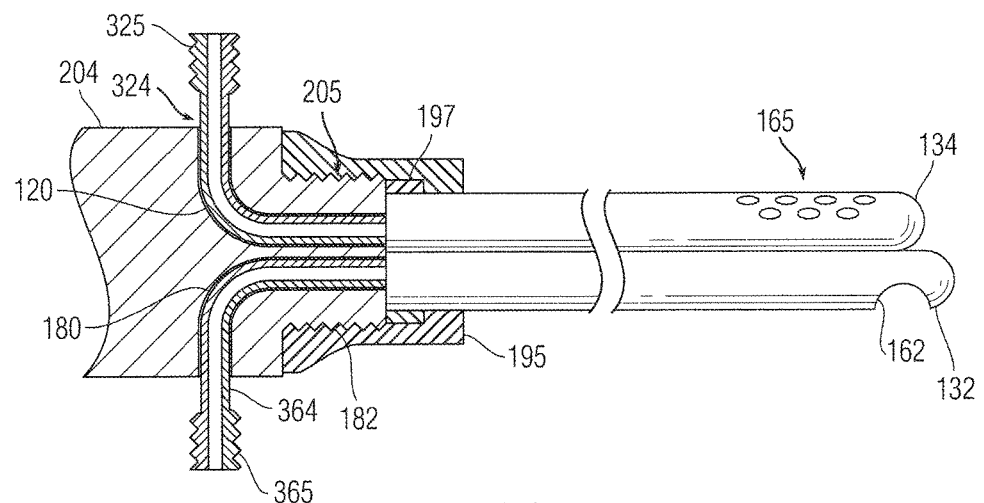
FIGS. 8A and 8B are views, partially in section, of a further embodiment of a surgical hand piece according to the present invention showing a change in the function of the dual lumens by rotation of the lumens within the hand piece.

A still further embodiment of a work tip for a hand piece according to the present invention is shown in FIG. 8A. As seen in FIG. 8A the connecting body 204 has passages 120, 180 as in the embodiment of FIG. 5A. However, in FIG. 8A the connecting body has a narrow section 205 on which there are the threads 182. Tubes 132 and 134 abut this narrow section of the connecting body, perhaps passing through O-rings, such as rings 193 in FIG. 5A, which are not shown in FIG. 8A so as to avoid obscuring the rest of the invention. A threaded collar 195 is slid over the tubes. An annular groove in collar 195 engages annular flanges 197 forming a hub at the proximal ends of the tubes. The collar also engages the threads 182. The narrow portion 205 of the connecting body and the proximal ends of the tubes each have alignment pieces (not shown) so that passages 120, 180 are aligned with the lumens in the tubes 132, 134. When the collar is tightened onto the threads 182 of the narrow part 205 of the connecting body, the engagement of the collar with the flanges 197 of the hub causes the tubes to be drawn into a tight stable connection with section 205.

Figure 8B:
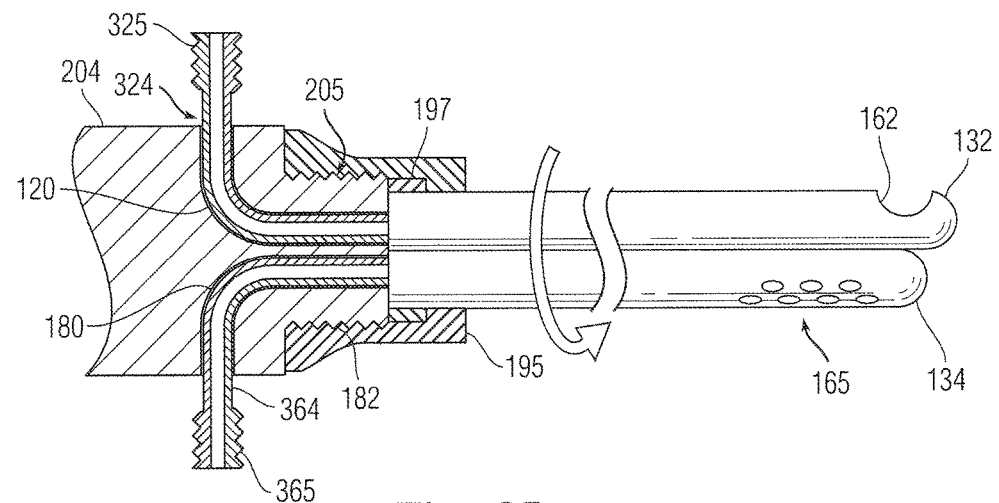

The distal ends of the tubes 132, 134 have, respectively, an enlarged opening 162 (typically used for aspiration) and a series of small openings 165 (typically used for a spray of infusion or irrigation fluid). If during the cleaning process the surgeon decides that the opening 162 would be better for spraying infusion fluid, the surgeon can loosen collar 195. This allows the surgeon to rotate the tubes 132, 134 in the hub with the flange 197, i.e., the annular flanges rotate in grooves of the collar as the tubes rotate. See the arrow in FIG. 8B. The alignment pieces engage when 180 degrees of rotation have occurred so that tube 134, which had been in connection with channel 120 is now in connection with channel 180, and tube 132, which had been in connection with channel 180 is now connected to channel 120. Thus, the infusion spray which had exited into the eye through holes 165, now enters the eye through the opening 162.

Plastic disposable tubes 324, 364 are provided. These disposable tubes can be inserted into the passages 120, 180 until their distal ends enter the two work tip tubes 132, 134. As a result, the tubes are made of a flexible material so that they can bend along the passages 120, 180. The proximal ends of tubes 132, 134 have O-rings or other sealing type openings which are made of a material softer than the disposable tubes so that these tubes can push through the seals into the tubes 132, 134 and form a fluid tight connection with them. Such seals can be of the type shown in FIG. 5, except they are located in the tubes 132, 134, instead of the connecting piece 204. The disposable tubes have connector 325, 365 at their proximal ends for connection to the source of irrigation (infusion) fluid or aspiration vacuum.

When the hand piece is used in its intended fashion and the procedure is over, the hand pieces can be quickly readied for use on another patient without the need for sterilization. In particular, the collar 195 is loosened. Then the working tip with tubes 132, 134 is disposed of. In addition, tubes 324, 364 are also disposed of. Each of these sets of tubes is replaced with clean, pre-sterilized tubes, and the hand piece is ready for the next use. This is possible because the only parts of the hand piece that come into contact with the aspiration fluid from the patient are the interiors of the tubes 132, 134 and 324, 364. As noted with respect to the embodiment of FIG. 5A, it may be useful in terms of expense to make the tubes 132, 134 of a material that is hard, but not as expensive as titanium, so as to be able to transmit the vibration force. The tubes 324, 364 do not have to transmit the vibration force, so they can readily be made of a plastic material such as TEFLON®, as a way of reducing the cost of the disposable parts of the hand piece.

The work tips of the invention, such as illustratively shown in FIGS. 1, 1A, 2, 5A, 5B, 8A and 8B, can be used with only an infusion/aspiration (I/A) function. That is, the source of ultrasonic energy can be turned off and only the aspiration and infusion/irrigation fluids supplied to the tubes 132 and 134. Also, the aspiration force can be lowered, e.g., from 500 mm Hg to 5-10 mm Hg during the cleaning operation so that the posterior capsule tissue at the back of the eye is not drawn into the tube. Here also the valve arrangement of FIG. 4 can be used so that either of the tubes can receive aspirated cortex tissue or supply irrigation fluid. However, it may be preferable to utilize the tube with the small circular holes 165 for this cleaning procedure, again to avoid aspirating the posterior capsule. Thus, the same instrument can be used for the phacoemulsification function while performing irrigation and aspiration as an operation takes place and also only for I/A functions (no ultrasonic energy is used) for cleaning the capsular bag as described above. This eliminates the need for the surgeon to change instruments and also provides the surgeon with a working tip having two tubes with different shape openings available for both aspiration and irrigation.

As indicated, the principals of the present invention can be applied to a versatile tool capable of ultrasonic phacoemulsification and infusion/aspiration cleanup. It was also noted that the tool can be used for phacoemulsification functions, withdrawn from the eye and replaced with an I/A tool designed only for cleanup and lacking an ultrasonic source. A typical prior art I/A tool 90 is shown in FIG. 9. It includes a handle 91 at one end and a removable infusion/aspiration tip 92 at the other end. FIG. 10 is an enlarged view of the prior art work tip. Unlike the present invention, the prior art tip has a source of infusion fluid 93 which fills a tube 96 which is concentric with an inner aspiration tube 95. At the distal end of the tip, there is an aspiration hole 94 in the inner tube 95 for collecting cells and bits of tissue during cleaning of the posterior capsule after a phacoemulsification procedure. The infusion fluid from inlet 93 exits from the distal end of outer infusion tube 96.

In a further embodiment of the present invention it is proposed to convert the concentric lumens structure of the prior art tool to a dual lumen work tip structure according to the present invention. A structure for accomplishing this is shown in FIG. 11. A dual lumen tip 300 for an I/A tool has a central lumen 305 for aspirating cells and tissue. This work tip 300 would connect with the aspiration flow pattern in a convention I/A device, such as that in FIG. 9. There is also a laterally located infusion lumen 306. In the device of FIG. 10 this lumen would be a cylindrical space that completely surrounds lumen 305. However, according to the present invention, it has its proximal end engage with an infusion inlet such as inlet 93 of FIG. 10, but it is formed as a lateral lumen next to lumen 305, as opposed to a cylindrical space surrounding lumen 305. The distal ends of the lumens can be provided with a variety of different holes in different patterns. For example, the holes 308 in tube 306 may be two elongated slots that form two sheets of fluid for sweeping the capsule surface. The holes 310 at the distal end of tube 305 may be rows of circular, triangular or other shaped holes. Depending on the configuration of holes that the surgeon desires, the roles of tubes 305 and 306 can be reversed by reversing the connection of the aspiration and infusion. Because of the offset relationship between tubes 305 and 306 with respect to the center axis of the tip, a mere rotation of that tip would not change the fluid flow paths.

There are at least four ways that the aspiration and infusion fluid functions can be switched at the end of the work tip. First, the surgeon can manually switch the aspiration and infusion tubes on the hand-piece. For this it would be helpful to have quick-disconnect connectors. However, even with such connectors, this approach would not be as quick as some other methods. Also, there could be fluid leakage during the switch and the surgeon might have to withdraw the tool from the patient's eye while the switch is made.

Second, a valve can be used to switch the fluid flow paths. Such a valve can be located inside the system console.

Third, the work piece can be constructed so that the dual lumen tubes can be rotated manually at the work tip as shown by FIGS. 5A, 5B, 8A and 8B. Such a method can be very fast and the surgeon need not look away from the surgical sight while the switch is made. Also, there is no need to withdraw the tool from the patient's eye during the switch.

Fourth, the aspiration and infusion tubes can be manually rotated about the lumens. In order to facilitate this rotation, a Teflon (or similar material) sleeve is fastened around the hand-piece. This 180° rotation will align the silicone aspiration and infusion tubes with the titanium infusion and aspiration lumens in the working tip.

Figure 12:
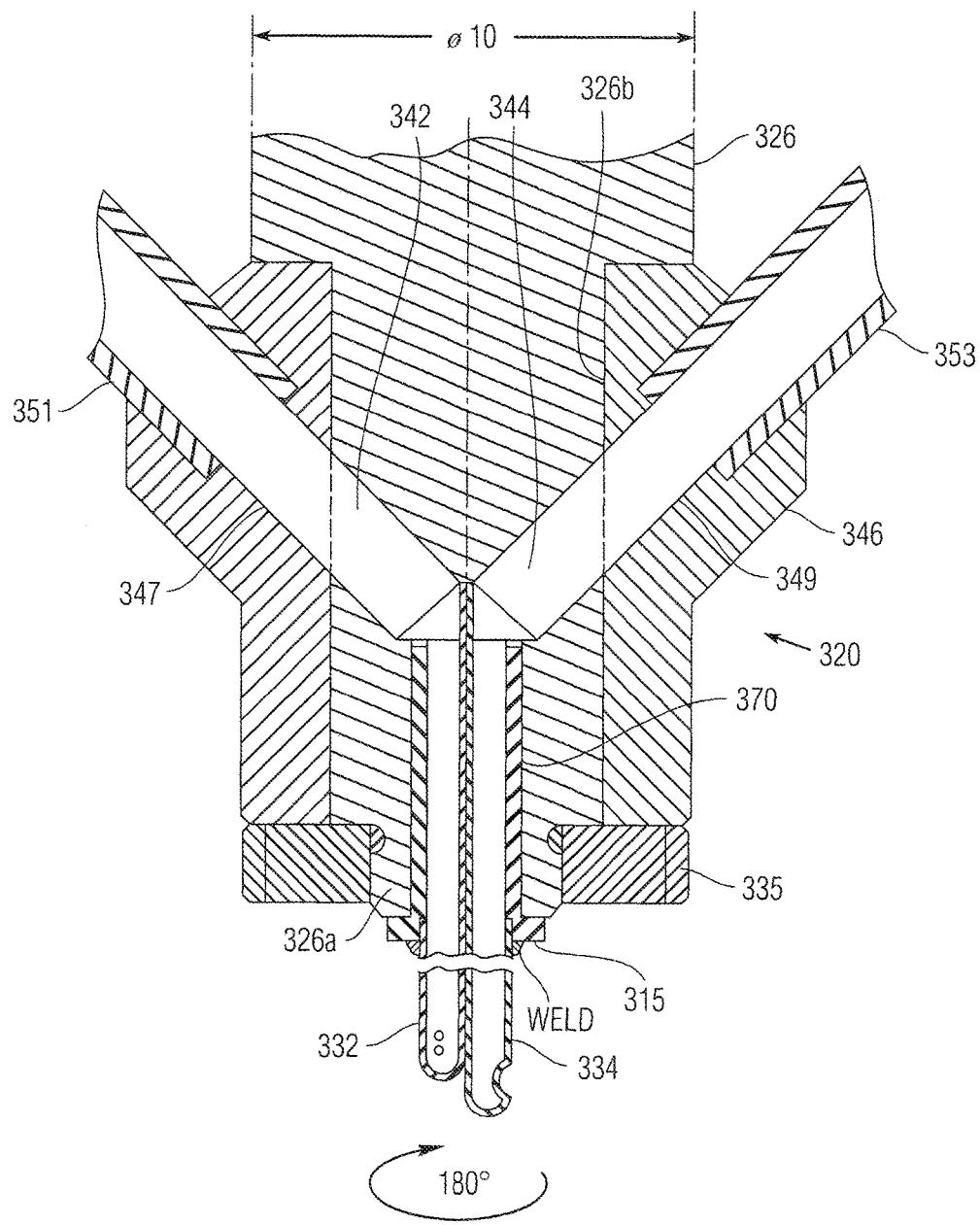
FIG. 12 is a cross section of a portion of a dual lumen surgical hand piece according to the present invention with a rotating nut for changing the function of the dual lumens within the hand piece.

FIG. 12 shows a tip 320 which is designed so that rotation of its lumens 332, 334 will change their function similar to the embodiments in FIGS. 5 and 8. The tip includes a body 326, which can be the connecting body of an ultrasonically driven phacoemulsification tool or simply the body of an I/A cleaning tool. Dual lumens 332, 334, typically made of titanium, are located in the distal end of the body 326. They are surrounded by a sleeve 370 acting as a hub that is threaded into a chamber in the distal end of body 326. A nut 315 is welded onto the sleeve 370. By turning the nut 315, e.g., with a wrench, the lumens can be securely fasted in the distal end of body 326. A threaded collar 335 attaches to the external distal reduced diameter end 326a of the body 326 and holds a sleeve 346 on the body in a reduced cross-sectional area 326b. The proximal end of lumen 332 is connected to a channel 342 in body 326 and the proximal end of lumen 334 is connected to a channel 344. These channels may also be made of titanium. Sleeve 346 has within it a channel 347, which is aligned with channel 342. Sleeve 346 also has a channel 349, which is aligned with channel 344. The channels 347 and 349 in the sleeve may be made of silicone or the entire sleeve 346 can be made of TEFLON®.

If the surgeon desires to swap the functions of the lumens 332, 334, the nut 315 is given a half turn, e.g., with a wrench, which causes the sleeve 370 to rotate and the alignment of lumen 332 with channel 342 to changed so that it now aligns with channel 344, and lumen 334 aligns with channel 342. Thus, the infusion and aspiration functions are swapped. The turning of nut 315 will cause a slight loosening of the sleeve 370 in the chamber of the body 326, but not a sufficient amount to cause fluid leakage. Further, if there is concern about such leakage, O-rings (not shown for the sake of clarity) can be placed about the proximal ends of each of the lumens. Detents and/or stops may be incorporated into the structure so that the surgeon can tell by feel when alignment of the lumens with the channels 342, 344 is achieved.

Figure 13:
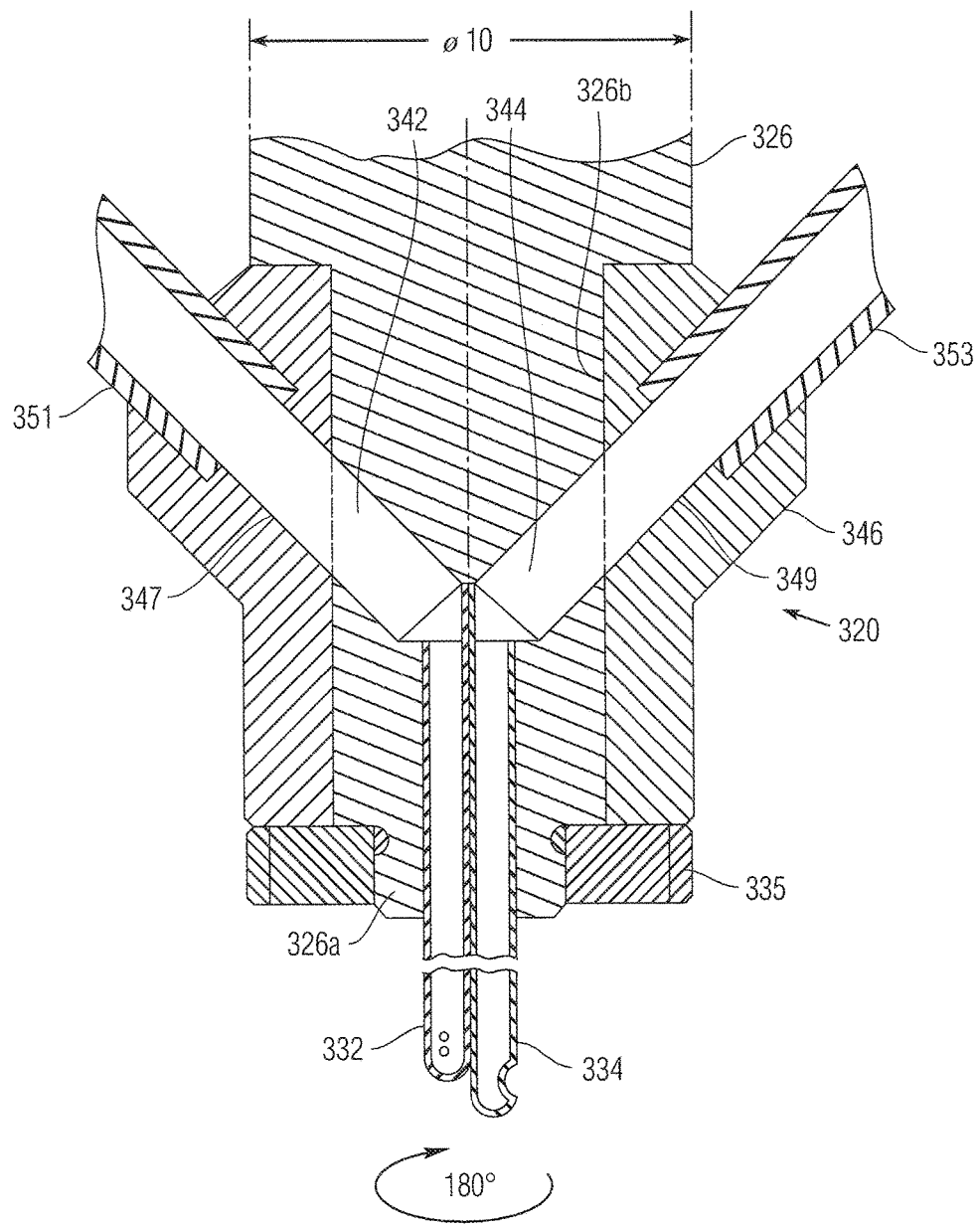
FIGS. 13 and 14 are cross sectional view of a portion of a dual lumen surgical hand piece according to the present invention with a rotatable exterior sleeve and showing a change in the function of the dual lumens by rotation of the sleeve.

FIG. 13 illustrates a still further embodiment. Like the arrangement of FIG. 12, it has a tip 320 that includes a body 326 which supports dual lumens 332, 334. The proximal end of lumen 332 is connected to a channel 342 in body 326 and the proximal end of lumen 334 is connected to a channel 344. A rotatable sleeve 346 surrounds a distal portion of body 326 of reduced cross section. Sleeve 346 is preferably made of a material that slides easily, e.g., TEFLON®, and it can be rotated about the body 326. Sleeve 346 has within it a channel 347, which in a first rotated position is aligned with channel 342. Sleeve 346 also has a channel 349, which in the first rotated position is aligned with channel 344 of lumen 334.

In the first rotated position infusion fluid enters channel 347 from an inlet 351. It travels into channel 342 and from there into lumen 332 so as to exit at the surgical site. Pieces of the cataract are aspirated by the suction force in lumen 334 and are drawn into channel 344. From channel 344 they pass into channel 349 in the sleeve to the aspiration outlet 353. If it is desired to reverse the functions of the lumens, the sleeve 346 is rotated about the body 324 to a second rotated position shown in FIG. 14. A detent or stop is provided so that sleeve 346 is retained in either the first or second rotated positions unless forced out of the position by manual force from the surgeon. In the second rotated position channel 342 of the body 326 is now aligned with channel 349 of the sleeve 346 and the aspiration outlet 353, while channel 344 is aligned with channel 347 and the infusion inlet 351. Typically the rotation from the first rotated position to the second can be 180 degrees. However, it can be more or less. Also, in a preferred embodiment the rotation from the first to the second position is in one direction and the rotation from the second to the first is in the opposite direction so that the infusion and aspiration tubes receive a half twist, but do not become completely twisted.

Figure 14:
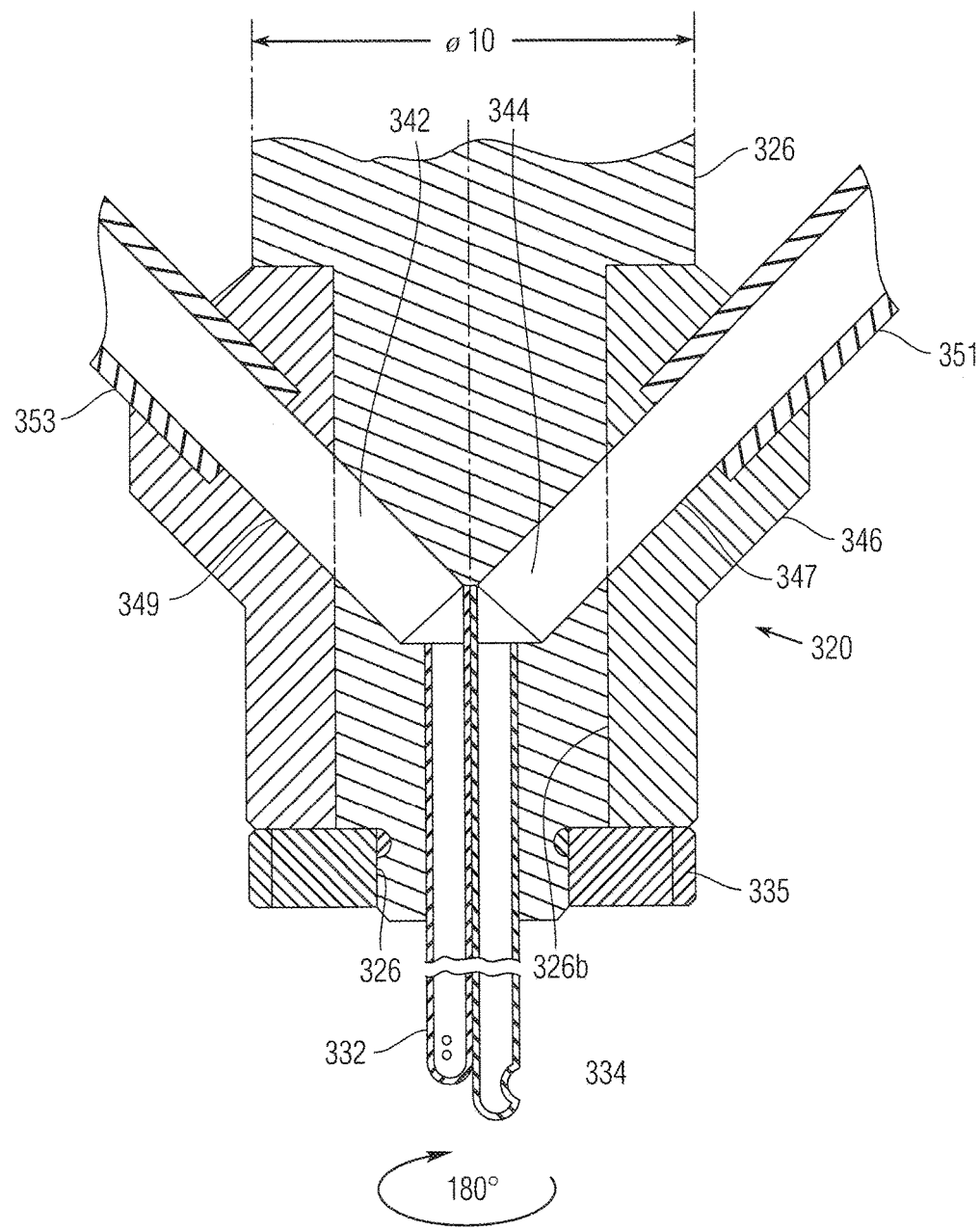
Figure 15A:
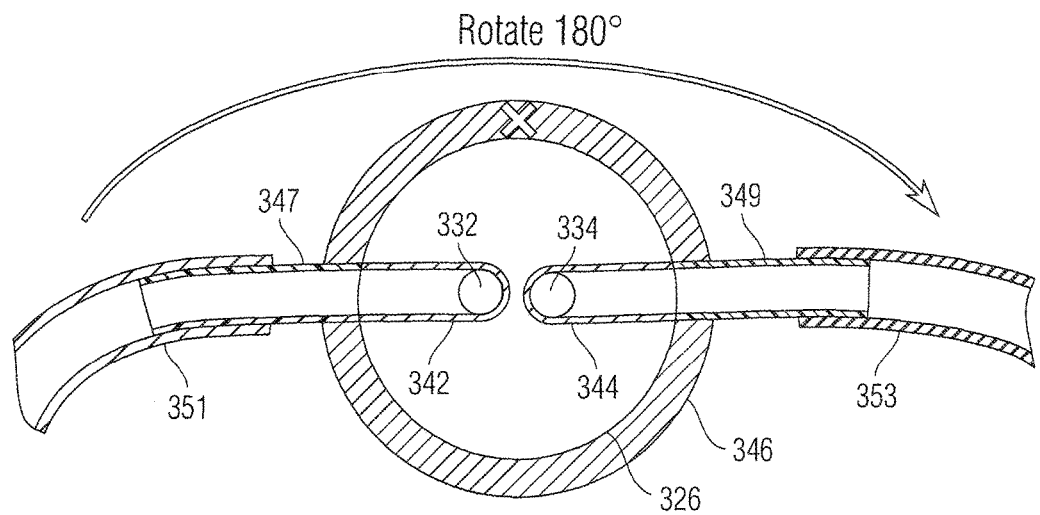
FIGS. 15A and 15B are cross sections of the hand piece in FIGS. 13 and 14 showing change in the position of the irrigation and aspiration tubes with rotation of the exterior sleeve.
Figure 15B:
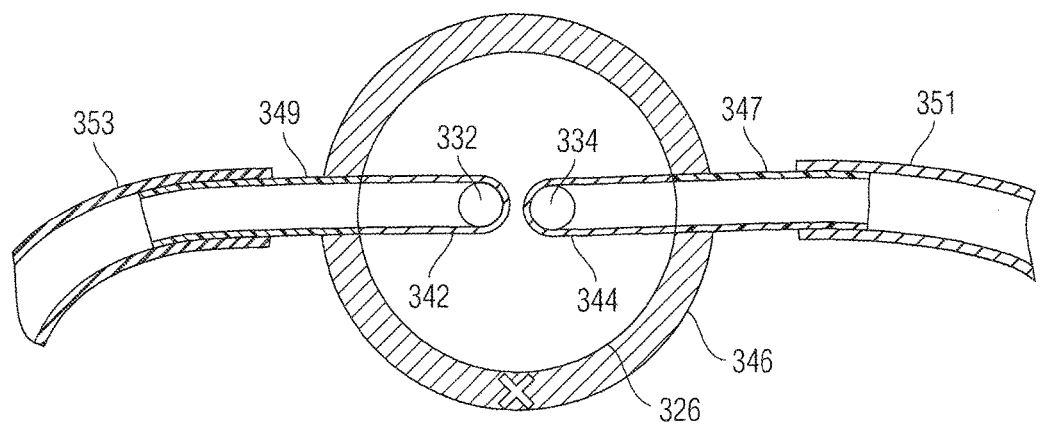

FIG. 15A is a cross section through the tip of FIG. 13 showing the arrangement in the first rotated position and FIG. 15B is a cross section through the tip of FIG. 14 showing the second rotated position. As can be seen in FIGS. 15A and 15B, in the first rotated position channel 342 of the body 326 is aligned with channel 347 of the sleeve 346 and the infusion inlet 351, while channel 344 is aligned with channel 349 and the aspiration inlet 353. In the second rotated position (FIG. 15B) the channel 342 of the body 324 is now aligned with channel 349 of the sleeve 346 and the aspiration outlet 353, while channel 344 is aligned with channel 347 and the infusion inlet 351.

Figure 16:
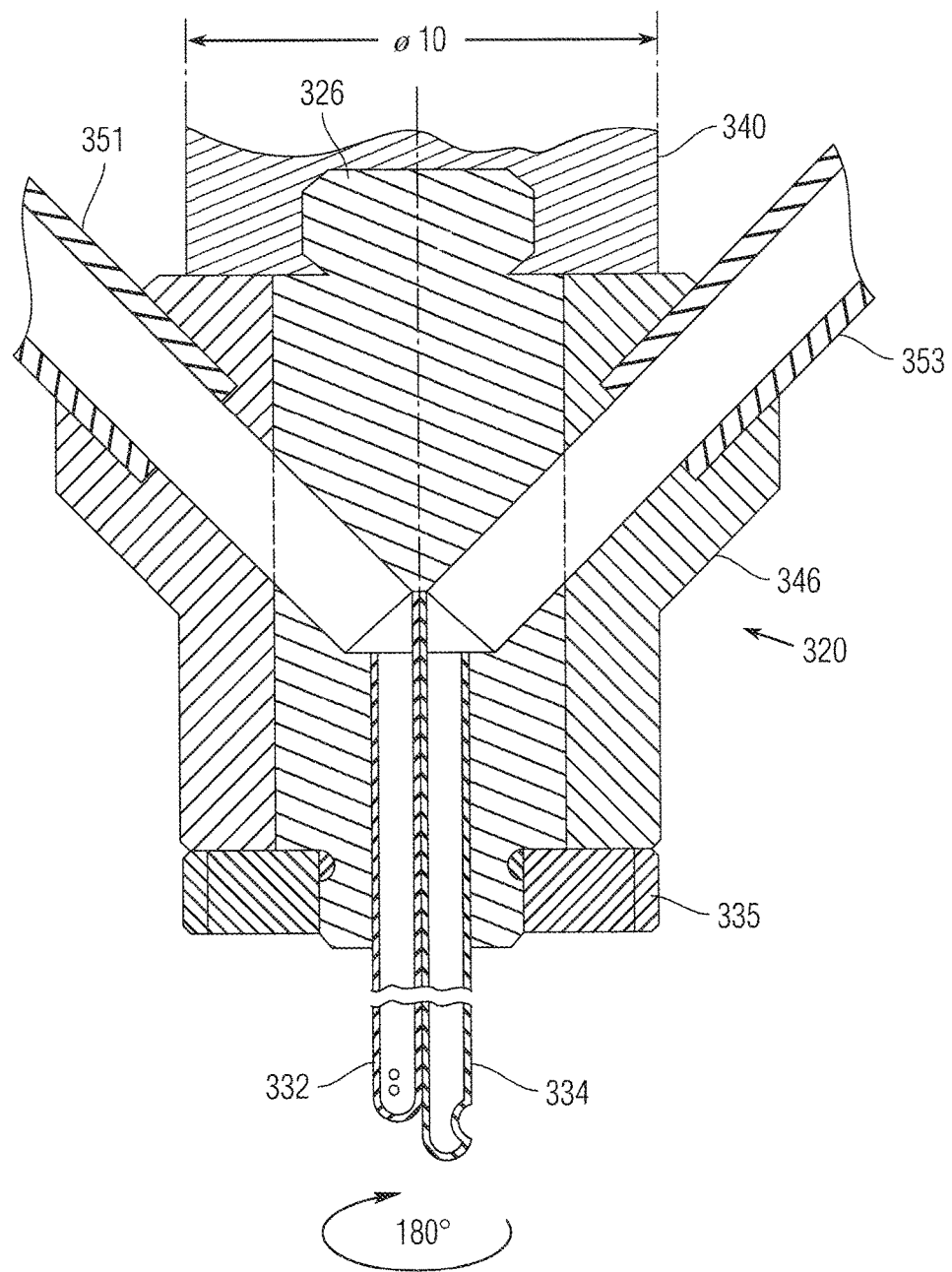
FIG. 16 is a cross-sectional view of a hand pieces with a rotatable external sleeve wherein a disposable work tip threaded into the connecting body.

FIG. 16 shows an arrangement similar to FIG. 13, except that the body 326 is connected by threads to a connecting body 340. After use, the input infusion line 351 and the aspiration outlet line 353 are disconnected. Then body 326 is unscrewed from body 340. The body 326 with lumens 332, 334 and the sleeve 346 are disposed of and are replaced with a new body with new lumens and a new sleeve. In this way the tool can be quickly readied for the next surgery without extensive sterilization.

Figure 17:
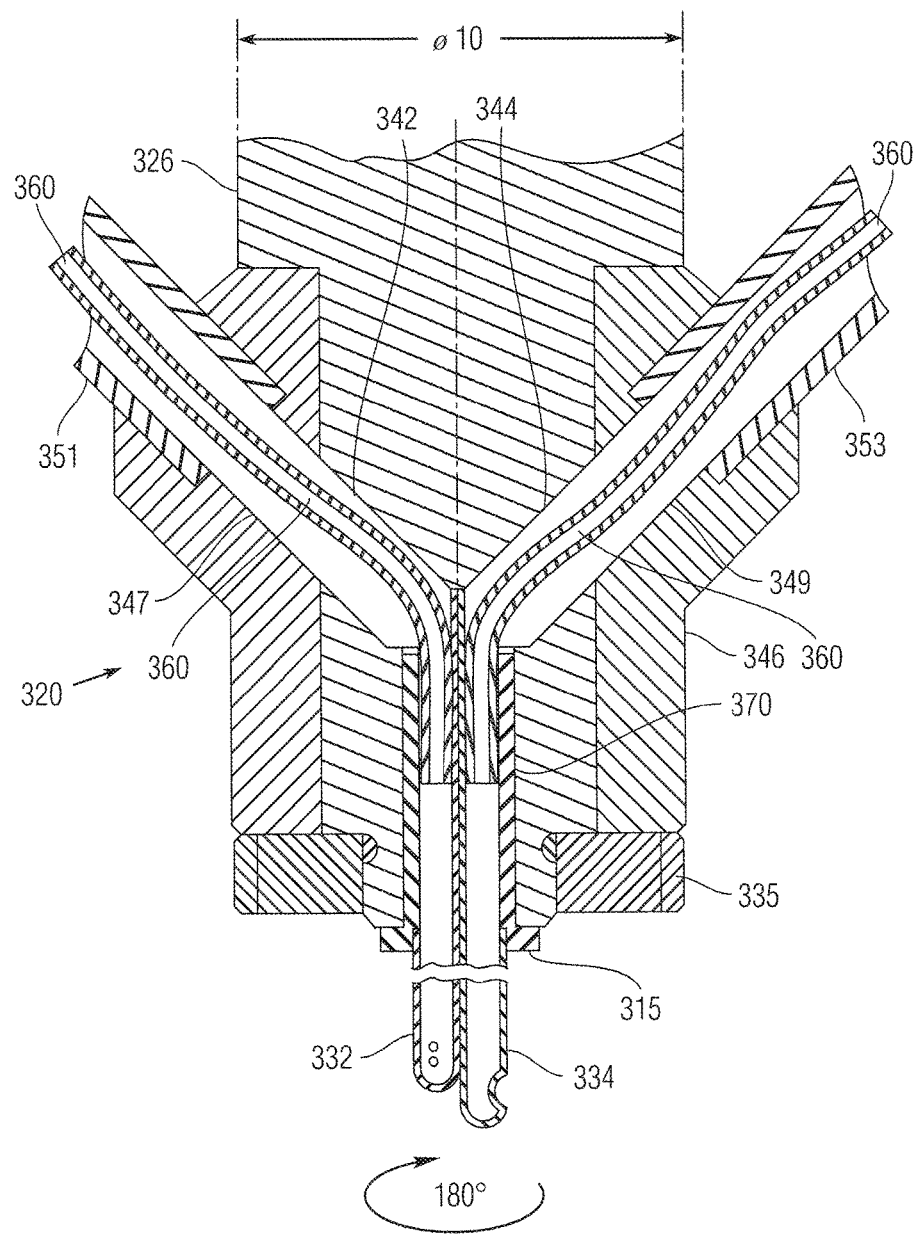
FIG. 17 is a cross-sectional view of a hand piece with rigid tubes press-fit into metal tubes in the work tip.

The embodiment of FIG. 17 is like FIG. 12, except that it includes disposable semi-rigid tubes 360 press-fit into the titanium tubes 342, 344 and titanium lumens 332, 334 in the work tip. The semi-rigid tubes can be discarded after an operation on a patient. If desired, the titanium tubes can be discarded after the operation, by turning nut 315 so that sleeve 370 with lumens 332, 334 can be detached. As a result, after a first operation is completed, another operation can be performed without having to sterilize the instrument. This is accomplished by replacing the semi-rigid tubes 360 and the sleeve assembly 370 with new sterile components. The semi-rigid tubes can be used in any embodiment to reduce the need for sterilization.

While the invention has been shown and described in connection with the removal of cataract from the eye of a patient, the apparatus and method may also be used for other types of surgery in other parts of the body, e.g., the removal of neurological tissue.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the scope of the appended claims.

I claim:

1. A surgical hand piece comprising:
a source of ultrasonic energy;
a connecting body having a proximal end connected to said ultrasonic energy source and a distal end;
a work tip for breaking up tissue having a proximal hub through which extend at least first and second tubes aligned side by side and adjacent to each other, said connecting body having first and second external openings, each of said at least first and second tubes having a proximal end connected to separate passages in said connecting body leading to the external openings connectable to respective first and second fluid sources,
said work tip being detachably connected to said connecting body distal end by a threaded collar threaded on to threads at the distal end of said connecting body,
wherein each of said at least first and second tubes has a lumen that is to receive or discharge a fluid at a proximal end of the tube from one of first and second fluid sources that are respectively irrigation and aspiration fluids, the lumen of each of said at least first and second tubes being separate and spaced apart, and each said at least first and second tube having an opening at distal end of the tube through which the fluid received at or discharged from the proximal end of the respective lumen of each said tube exits from or enters the tube, with each said tube distal end opening being separate, independent of, spaced from and without being in communication with the distal end opening of the other tube; and
wherein the lumens of said work tip and the first and second fluid sources are rotatable with respect to each other so that in one operative position the first tube is in fluid communication with the first fluid source and the second tube is in fluid communication with the second fluid source, and in another operative position the first tube is in fluid communication with the second fluid source and the second tube is in fluid communication with the first fluid source.

2. The surgical hand piece according to claim 1 wherein the openings at the distal ends of the at least first and second tubes are different in size, shape or number of holes on the first tube with respect to the second tube.

3. The surgical hand piece according to claim 1 wherein the opening at the distal end of at least one of said at least first and second tubes is formed by a hollow work-tip end, the interior wall of said hollow work-tip end having a first diameter toward the distal end of the hollow work-tip end and a second section toward the proximal end with a diameter less than that of the first section, said first and second sections being connected by a transition section defining an angled surface between the first and second sections, an opening at the distal end of the tube with the first diameter being at an acute angle to the axis of the tube, the ultrasonic vibratory energy being transmitted within said hollow end from the second section to the first.

4. The surgical hand piece according to claim 3 wherein the exterior surface of said hollow work-tip end is of the same general shape as the interior.

5. The surgical hand piece according to claim 1 wherein said collar includes an annular internal recess and internal threads,
the first and second fluid sources are connected to separate passages in the connecting body that extend to a distal face of the connecting body,
the outer surface of the distal end of the connecting body is threaded,
the first and second external openings for the at least first and second tubes are in an end face of the proximal hub and the proximal hub has an annular projection in its outer circumference, and
the projection of the proximal hub extends into the recess of the collar and the internal threads engage the distal threads of the connecting body so that the external openings for the at least first and second tubes are aligned with and adjacent to the passages in the connecting body, whereby when the collar is loose, the proximal hub with the at least first and second tubes can rotate with respect to the passages in the end face of the connecting body, and when the collar is threaded tight, the tubes are fixed with respect to the connecting body passages.

6. The surgical hand piece according to claim 5 further including a sealing means located where the at least first and second tubes are aligned with and adjacent to the passages in the connecting body, said sealing means sealing the connection between the tubes and passages throughout any rotation with respect to each other.

7. The surgical hand piece according to claim 6 further including a source of ultrasonic energy connected to a proximal end of the connecting body.

8. A surgical hand piece comprising:
a connecting body having a distal end;
a work tip having a proximal hub through which extend at least first and second tubes aligned side by side and adjacent to each other, said connecting body having first and second external openings, each of said at least first and second tubes having a proximal end connected to separate passages in said connecting body leading to the external openings connectable to respective first and second fluid sources,
said work tip being detachably connected to said connecting body distal end by a threaded collar threaded on to threads at the distal end of said connecting body,
wherein each of said at least first and second tubes has a lumen that is to receive or discharge a fluid at a proximal end of the tube from one of first and second fluid sources that are respectively irrigation and aspiration fluids, the lumen of each of said at least first and second tubes being separate and spaced apart, and each said tube having an opening at a distal end of the tube through which the fluid received at or discharged from the proximal end of the respective lumen of each said tube exits from or enters the tube, with each said tube distal end opening being separate, independent of, spaced from and without being in communication with the distal end opening of the other tube;
wherein the lumens of said work tip and the first and second fluid sources are rotatable with respect to each other so that in one operative position the first tube is in fluid communication with the first fluid source and the second tube is in fluid communication with the second fluid source, and in another operative position the first tube is in fluid communication with the second fluid source and the second tube is in fluid communication with the first fluid source;
wherein said collar includes an annular flange and internal threads,
wherein the first and second fluid sources are connected to the separate passages in the connecting body that extend to a distal face of the connecting body,
wherein the outer surface of the distal end of the connecting body is threaded,
wherein the first and second external openings for the at least first and second tubes are in an end face of the proximal hub and the proximal hub has an annular groove in its outer circumference, and
wherein the flange of the collar extends into the groove of the proximal hub and the internal threads engage the distal threads of the connecting body so that the external openings for the at least first and second tubes are aligned with and adjacent to the passages in the connecting body, whereby when the collar is loose, the proximal hub with the at least first and second tubes can rotate with respect to the passages in the end face of the connecting body, and when the collar is threaded tight, the tubes are fixed with respect to the connecting body passages.

9. The surgical hand piece according to claim 8 further including a sealing means located where the at least first and second tubes are aligned with and adjacent to the passages in the connecting body, said sealing means sealing the connection between the tubes and passages throughout any rotation with respect to each other.

10. The surgical hand piece according to claim 9 further including a source of ultrasonic energy connected to a proximal end of the connecting body.

11. A surgical hand piece comprising:
a source of ultrasonic energy;
a connecting body having a proximal end connected to said ultrasonic energy source and a distal end;
a work tip for breaking up tissue having a proximal hub from which extend at least first and second tubes aligned side by side and adjacent to each other, each of said at least first and second tubes having a proximal end selectively connectable to separate first and second passages in said connecting body which lead to external openings connected to first and second fluid sources, said proximal hub being detachably connected to said connecting body distal end by means of threads on the proximal hub, each of said at least first and second tubes has a lumen that is to receive or discharge a fluid at a proximal end of the tube from one of the first and second passages, which fluids are respectively irrigation and aspiration fluids, the lumen of each of said at least first and second tubes being separate and spaced apart, and each said tube having an opening at a distal end of the tube through which the fluid received at or discharged from the proximal end of the respective lumen of each said tube exits from or enters the tube, with each said tube distal end opening being separate, independent of, spaced from and without being in direct communication with the distal end opening of the other tube; and wherein the lumens of said work tip with their proximal hub and the first and second passages are rotatable with respect to the fluid passages so that in one operative position the first tube is in fluid communication with the first fluid source and the second tube is in fluid communication with the second fluid source, and in another operative position the first tube is in fluid communication with the second fluid source and the second tube is in fluid communication with the first fluid source.

12. The surgical hand piece according to claim 11 further including a nut fixed to the proximal hub at the distal end thereof so as to promote manual rotation of the work tip.

13. The surgical hand piece according to claim 11 further including a sealing means located where the at least first and second tubes are aligned with and adjacent to the first and second passages in the connecting body, said sealing means sealing the connection between the at least first and second tubes and channels throughout any rotation with respect to each other.

14. The surgical hand piece according to claim 11 further including a source of ultrasonic energy connected to a proximal end of the connecting body.

15. The surgical hand piece according to claim 11 further including disposable semi-rigid tubes press-fit into the first and second passages in said connecting body, whereby after a surgical procedure the work tip and the semi-rigid tubes can be replaced with new pieces and the hand piece can be used for another surgery without sterilization.

16. A surgical hand piece comprising:
a source of ultrasonic energy;
a connecting body having a proximal end connected to said ultrasonic energy source and a distal end;
first and second tubes located toward the distal end of the connecting body and aligned side by side and adjacent to each other for breaking up tissue, each of said first and second tubes having a proximal end connectable to separate first and second passages in said connecting body leading to external openings from said body,
a sleeve mounted on a first reduced diameter portion of the connecting body, first and second fluid passages in said sleeve connected between first and second fluid sources and the first and second passages in said connecting body,
a collar threaded on to a second reduced diameter portion of the connecting body and supporting the sleeve when tightened, but when loose the sleeve is rotatable about the first reduced diameter portion of the connecting body,
each of said first and second tubes has a lumen that is to receive or discharge a fluid at a proximal end of the tube from one of the first and second passages, which fluids are respectively irrigation and aspiration fluids, the lumen of each of said first and second tubes being separate and spaced apart, and each said tube having an opening at a distal end of the tube through which the fluid received at or discharged from the proximal end of the respective lumen of each said tube exits from or enters the tube, with each said tube distal end opening being separate, independent of, spaced from and without being in communication with the distal end opening of the other tube; and wherein the sleeve along with the first and second fluid passages as well as the first and second fluid sources can be rotated about the first reduced diameter portion of the connecting body so that in one operative position the first tube and the first passage of the connecting body are in fluid communication with the first fluid passage of the sleeve and the first fluid source, and the second tube and the second passage of the connecting body are in fluid communication with the second fluid passage of the sleeve and the second fluid source, while in another operative position the first tube and the first passage of the connecting body are in fluid communication with the second fluid passage of the sleeve and the second fluid source, and the second tube and the second passage of the connecting body are in fluid communication with the first fluid passage of the sleeve and the first fluid source.

17. The surgical hand piece according to claim 16, wherein the sleeve is made of a material that facilitates rotation.

18. The surgical hand piece according to claim 17, wherein the sleeve is made of TEFLON®.

19. The surgical hand piece according to claim 16, wherein the connecting body has a proximal section and a distal section connected together by a threaded connection, whereby after a surgical procedure the fluid sources can be disconnected and distal section with the lumens and sleeve can be replaced with new pieces and the hand piece can be used for another surgery without sterilization.

20. A surgical hand piece comprising:
a source of ultrasonic energy;
a connecting body having a proximal end connected to said ultrasonic energy source and a distal end, said connecting body transmitting the ultrasonic energy to its distal end;
a work tip for breaking up tissue having a proximal hub adjacent the distal end of the connecting body and from which extend at least first and second tubes aligned side by side and adjacent to each other, said proximal hub having first and second external openings, each of said tubes having a proximal end connected to separate passages in said proximal hub leading to the external openings, said proximal hub and tubes being vibrated together by said connecting body;

wherein each of said at least first and second tubes has a lumen that is to receive or discharge a fluid at a proximal end of the tube from one of first and second fluid sources that are respectively irrigation and aspiration fluids, the lumen of each of said at least first and second tubes being separate and spaced apart, and each said tube having an opening at a distal end of the tube through which the fluid received at or discharged from the proximal end of the respective lumen of each said tube exits from or enters the tube, with each said tube distal end opening being separate, independent of, spaced from and without being in communication with the distal end opening of the other tube; and wherein the work tip is detachable from the connecting body while leaving the connection body attached to said hand piece, and the work tip is designed to be disposed of after a single use.

21. The surgical hand piece according to claim 20 further including passages in the connecting body.

22. A work tip for a surgical hand piece comprising:
a connecting body having a distal end;
a proximal hub adapted to be ultrasonically vibrated by a distal end of a connecting body of the hand piece; and
at least first and second tubes extending from within said proximal hub and being aligned side by side and adjacent to each other so that the at least first and second tubes vibrate with the proximal hub, said proximal hub having first and second external openings connectable to respective first and second fluid sources, each of said at least first and second tubes having a proximal end connected within the proximal hub to separate ones of the external openings;
wherein said work tip is adapted to be detachably connected to the connecting body distal end;
wherein each of said at least first and second tubes has a lumen that is to receive or discharge a fluid at a proximal end of the tube from one of first and second fluid sources that are respectively irrigation and aspiration fluids, the lumen of each of said at least first and second tubes being separate and spaced apart, and each said tube having an opening at a distal end of the tube through which the fluid received at or discharged from the proximal end of the respective lumen of each said tube exits from or enters the tube, with each said tube distal end opening being separate, independent of, spaced from and without being in communication with the distal end opening of the other tube; and
whereby, after a surgical procedure, the fluid sources can be disconnected, the proximal hub with the lumens can be replaced with new pieces and the hand piece can be used for another surgery without sterilization.

23. A surgical hand piece comprising:
a connecting body having a distal end;
a work tip having a proximal hub through which extend at least first and second tubes aligned side by side and adjacent to each other, said connecting body having first and second external openings, each of said tubes having a proximal end connected to separate passages in said connecting body leading to the external openings which are connectable to respective first and second fluid sources,
disposable semi-rigid tubes press-fit into the separate passages in said connecting body;
said work tip being detachably connected to said connecting body distal end by a threaded collar threaded on to threads at the distal end of said connecting body,
wherein each of said at least first and second tubes has a lumen that is to receive or discharge a fluid at a proximal end from one of said first and second fluid sources that are respectively irrigation and aspiration fluids, the lumen of each of said at least first and second tubes being separate and spaced apart, and each said tube having an opening at a distal end through which the fluid received at or discharged from the proximal end of the respective lumen of each said tube exits from or enters the tube, with each said tube distal end opening being separate, independent of, spaced from and without being in communication with the distal end opening of the other tube; and
whereby, after a surgical procedure, the fluid sources can be disconnected, the proximal hub with the lumens and the disposable semi-rigid tubes can be replaced with new pieces, and the hand piece can be used for another surgery without sterilization.

\* \* \* \* \*